(12) United States Patent
Chitre et al.

(10) Patent No.: US 7,058,454 B1
(45) Date of Patent: Jun. 6, 2006

(54) STIMULATION/SENSING ELECTRODES FOR USE WITH IMPLANTABLE CARDIAC LEADS IN CORONARY VEIN LOCATIONS

(75) Inventors: Yougandh Chitre, Valencia, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 602 days.

(21) Appl. No.: 10/232,866

(22) Filed: Aug. 30, 2002

(51) Int. Cl.
*A61N 1/05* (2006.01)

(52) U.S. Cl. .......................... 607/116; 257/4

(58) Field of Classification Search ........... 607/122, 607/119, 121, 116, 123, 148; 257/4
See application file for complete search history.

(56) References Cited

U.S. PATENT DOCUMENTS

| | | | | |
|---|---|---|---|---|
| 4,341,226 A | * | 7/1982 | Peters | 607/132 |
| 4,603,704 A | | 8/1986 | Mund et al. | 128/784 |
| 4,611,604 A | | 9/1986 | Botvidsson et al. | 128/784 |
| 5,383,922 A | | 1/1995 | Zipes et al. | 607/122 |
| 5,587,200 A | | 12/1996 | Lorenz et al. | 427/2.24 |
| 5,755,761 A | | 5/1998 | Obino | 607/122 |
| 5,999,858 A | | 12/1999 | Sommer et al. | 607/122 |
| 6,144,882 A | | 11/2000 | Sommer et al. | 607/125 |
| 6,161,029 A | | 12/2000 | Spreigl et al. | 600/381 |
| 6,256,542 B1 | * | 7/2001 | Marshall et al. | 607/126 |
| 6,295,475 B1 | | 9/2001 | Morgan | 607/122 |
| 2001/0000800 A1 | * | 5/2001 | Partridge et al. | 607/130 |
| 2001/0032005 A1 | * | 10/2001 | Gelb et al. | 607/121 |
| 2002/0072787 A1 | | 6/2002 | Partridge et al. | 607/122 |

FOREIGN PATENT DOCUMENTS

WO   WO 01/02053   1/2001

* cited by examiner

*Primary Examiner*—Jeffrey R. Jastrzab
*Assistant Examiner*—Fernando Aguel

(57) ABSTRACT

A lead assembly for a body implantable medical system adapted to transmit electrical signals between proximal and distal end portions of the lead assembly to thereby stimulate selected body tissue includes an electrical conductor, an insulative sheath composed of silicone or polyurethane covering the conductor, an electrical connector coupled to the proximal end of the conductor for releasable attachment to a stimulating pulse generator and a distal electrode coupled to the distal end of the conductor. The distal electrode has an outer surface generally coaxial with the lead assembly and facing transversely of the longitudinal axis of the lead assembly and generally parallel to the selected body tissue intended for stimulation. The outer surface of the distal electrode is composed of a biocompatible metallic alloy and includes a layer of a material that exhibits low polarization and thereby enhances the electrical efficacy of the electrode.

10 Claims, 8 Drawing Sheets

STIMULATION/SENSING ELECTRODES FOR USE WITH IMPLANTABLE CARDIAC LEADS IN CORONARY VEIN LOCATIONS

FIELD OF THE INVENTION

The present invention relates generally to lead assemblies for connecting implantable medical devices with selected body tissue to be stimulated by such devices, and more particularly to stimulating electrodes for use with such lead assemblies designed to provide optimized stimulation of the body tissue.

BACKGROUND OF THE INVENTION

Implantable cardiac devices are commonly used for treating patients with heart arrhythmias. These devices include well-known pacemakers and implantable cardioverter defibrillators (ICD's). In general, these devices include a lead that is adapted to be implanted in the body of the patient so as to be positioned adjacent the heart and a control unit that is also adapted to be implanted within the patient which is connected to the lead so as to deliver electrical impulses to the heart via the lead. Pacemaker devices can be very sophisticated and include sensors and processing capabilities so that pacing is provided only when needed.

In pacing applications, the lead is typically implanted within the chambers of the heart so as to be positioned adjacent the walls of the right atrium or the right ventricle. In many typical pacemakers, the leads are implanted so that the lead is positioned within the right atrium and the right ventricle chambers so that a pacing pulse can be delivered directly to cardiac cells of these chambers to induce a paced response of the heart.

There are several different types of leads that are currently in common use in pacing applications. One very common lead is a bipolar lead which includes a pacing cathode electrode and an anode electrode. The same two electrodes also serve to sense cardiac signals. The pacing pulse is delivered to the cardiac cells by the cathode and anode electrodes. Typically, the sensing by the same two electrodes is configured so as to monitor intrinsic heart activity and provide a signal indicative thereof to the control unit. Other types of leads include unipolar leads which have a single (cathode) electrode for delivering stimulation pulses to the heart and an indifferent (anode) electrode, such as the casing of the control unit which serves as the return electrode for the stimulation pulses.

As discussed above, pacemaker electrodes are typically implanted within the right atrium and right ventricle. The right atrium and the right ventricle generally provide blood circulation to the pulmonary system, i.e., circulation to the heart itself. The left atrium and the left ventricle provide circulation to the rest of the body's circulatory system including the major organs of the body such as the brain. Typically, implantation within the right atrium and the right ventricle has been preferred to implanting leads within the left atrium and the left ventricle, which has generally been thought to be too invasive of a procedure and to pose undesirable risks of complications to the flow of blood in the circulatory system. However, as the blood in the circulatory system is so primarily pumped by the left atrium and the left ventricle, pacing the right atrium and the right ventricle may not always provide optimum results in ensuring adequate cardiac activation and hemodynamics.

Consequently, there has been a desire to develop techniques for pacing the left atrium and the left ventricle. One such technique involves the implantation of transvenous leads into the coronary sinus region via the right atrium. As used herein, the phrase "coronary sinus region" refers to the coronary sinus vein, great cardiac vein, left marginal vein, left posterior ventricular vein, middle cardiac vein, and/or small cardiac vein or any other cardiac vein accessible by the coronary sinus.

The coronary sinus is a vein in the coronary circulatory system that is typically located in the heart so as to be proximal the outer walls of the left atrium and left ventricle of the heart. The coronary sinus vein opens into the right atrium through the coronary ostium (or Os), that is accessible for lead implantation. By implanting a lead within the coronary sinus region and then positioning the lead tip so that the lead's electrodes are adjacent the left atrium or the left ventricle, it is known that stimulation pulses can be provided to the left atrium or the left ventricle. This allows these chambers to be paced, resulting in improved activation without the complications associated with directly implanting leads within these chambers.

Current left heart pacing leads whose stimulation electrodes are positioned in the coronary veins, for example, are simple in design, such as a ring, partial ring, or a tip electrode. However, none of these electrode designs are designed specifically for achieving optimal electrode-tissue orientation to achieve (in turn) optimal cardiac stimulation thresholds in the coronary veins. They are not able to perform optimally as the electrodes for these leads are not able to provide electrical fields that are optimally directed towards excitable cardiac tissue.

A number of patents are typical of the prior art in this regard. U.S. Pat. No. 5,383,922 to Zipes et al. discloses an implantable lead system that includes RF electrodes for fixating the lead into position. U.S. Pat. No. 5,755,761 to Obino discloses an implantable lead system that includes partial ring electrodes for changing the delivery of the pulse. U.S. Pat. Nos. 5,999,858 and 6,144,882 to Sommer et al. and U.S. Pat. No. 6,295,475 to Morgan each discloses an implantable lead system that has a shaped tip electrode. U.S. Pat. No. 6,161,029 to Spreigl et al. discloses an implantable lead system that includes a stent-like distal electrode.

It was with knowledge of the foregoing state of the technology that the present invention has been conceived and is now reduced to practice.

SUMMARY

The present invention, then, relates to a lead assembly for a body implantable medical system adapted to transmit electrical signals between proximal and distal end portions of the lead assembly to thereby stimulate selected body tissue. The lead assembly of the invention includes an electrical conductor, an insulative sheath composed of silicone or polyurethane covering the conductor, an electrical connector coupled to the proximal end of the conductor for releasable attachment to a stimulating pulse generator and a distal electrode coupled to the distal end of the conductor. The distal electrode has an outer surface generally coaxial with the lead assembly, and faces transversely of the longitudinal axis of the lead assembly, and generally lies parallel to the selected body tissue intended for stimulation. The outer surface of the distal electrode is composed of a biocompatible metallic alloy and includes a layer of a material that exhibits low polarization and thereby enhances the electrical efficacy of the electrode.

It has been found that at locations of the distal electrode at which discontinuities occur, such as an interface between the electrode and the insulation sheath, or at corners or edges demarking the interface between adjacent transverse surfaces of the electrode, a concentration of the electrical charge occurs which creates a concentrated electrical field and substantially improves the effectiveness of the stimulation directed to the selected body tissue.

The distal electrode may be of any one of a variety of shapes and is composed of a biocompatible metallic alloy. Whatever shape is employed, the outer surface of the distal electrode includes a layer of a material such as titanium nitride (TiN) that exhibits low polarization and thereby enhances the electrical efficacy of the electrode. In this regard, the entire disclosure of commonly-assigned U.S. Patent Application of Yougandh Chitre and Phong D. Doan, entitled "Stimulating Electrode Having Low Polarization and Method of Making Same," Ser. No. 09/707,828, filed Nov. 7, 2000, is incorporated herein by reference. Other commonly-assigned patents which disclose earlier electrode technology achievements of this type include U.S. Pat. No. 4,603,704 to Mund et al.; U.S. Pat. No. 4,611,604 to Botvidsson et al.; and U.S. Pat. No. 5,587,200 to Lorenz et al.

As explained in the disclosure of that application, polarization, is an artifact that results from the accumulation of charge at the electrode/tissue interface post-stimulation. This after-potential prevents the accurate sensing of intrinsic cardiac electrical activity. Up to the time of the Chitre and Doan invention, electrodes of both the tip and ring variety often employed a surface coating of titanium nitride (TiN). The implementation of TiN as a coating material of choice had earlier provided a breakthrough in the pacing industry by exhibiting properties of corrosion resistance and providing an interface with increased electrode/tissue capacitance. The increase in interface capacitance is a result of the increased active surface area brought about by the fractal morphology of the sputter coated titanium nitride material. However, the increase in interface capacitance, in turn, lowers the polarization artifact typically seen following the pacing pulse. Attempts to counter this result were generally unsatisfactory until the development of the electrode of that invention which exhibits an initially exposed outer surface substantially covered with a first inner layer of titanium nitride and a second outer layer of platinum black. In this instance, the first inner layer of titanium nitride has a thickness of less than about 15 microns and the second outer layer of platinum black overlying the layer of titanium nitride, similarly, has a thickness of less than about 15 microns.

A primary feature, then, of the present invention is the provision of a stimulating electrode for use with an associated lead assembly designed to provide optimized stimulation of the body tissue.

Another feature of the present invention is the provision of such optimal stimulating electrode designs which provide significantly improved electrical field distribution directed towards excitable cardiac tissue in a coronary vein.

Still another feature of the present invention is the provision of such a stimulating electrode which effectively reduces the losses of electrical current occurring in the blood stream.

Yet another feature of the present invention is the provision of such a stimulating electrode which provides enhanced stability of the electrode at the tissue stimulation site.

Still a further feature of the present invention is the provision of such a stimulating electrode for use with an associated lead assembly having low polarization which results in lower capture thresholds, increased sensing thresholds, and clearer evoked response signals.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DESCRIPTION OF THE PREFERRED EMBODIMENTS

Figure 1:
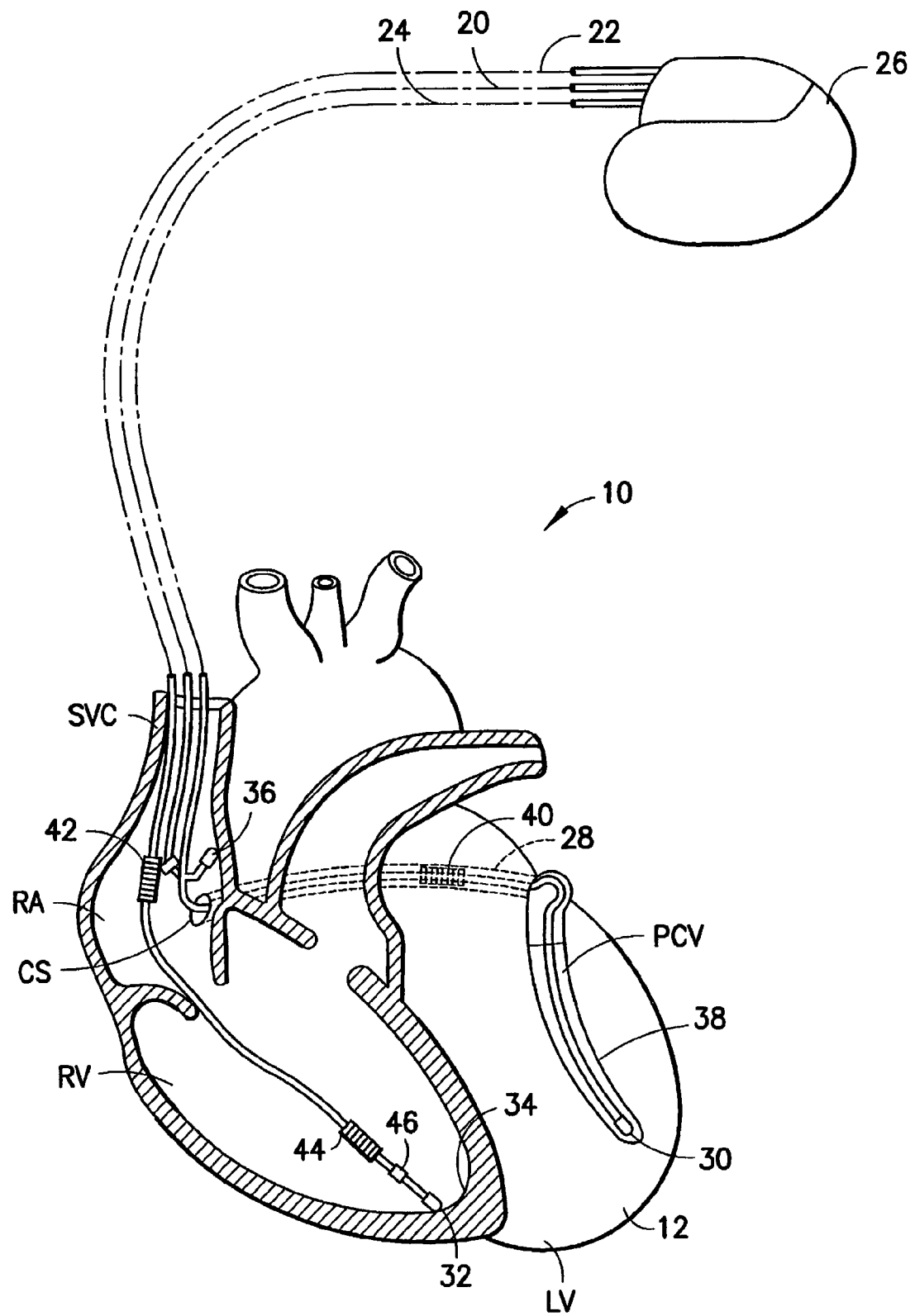
FIG. 1 is a diagrammatic perspective view illustrating an implanted lead system for providing electrical stimulation of a heart employing an implantable lead embodying the present invention.

Refer now to the drawings and, initially, to FIG. 1 in which is shown a diagrammatic perspective view of an implanted system 10 for providing electrical stimulation of a heart 12 incorporating features of the present invention. Although the present invention will be described with reference to the embodiments shown in the drawings, it should be understood that the present invention can be embodied in many alternate forms or embodiments. In addition, any suitable size, shape or type of elements or materials consistent with, and suitable for, the invention could be used.

In FIG. 1, there are also illustrated implantable leads 20, 22, 24 generally embodying the invention for stimulation of the body, the heart 12 in this instance, by means of a pacemaker 26 or other suitable pulse generating device. This is a cross-section view of a human heart showing the right atrium (RA) and the right ventricle (RV) along with the coronary sinus CS and a vein 28 of the left side of the heart. This vein of the left side could be any of the veins found on the left side of the heart such as the Great Cardiac Vein, Posterior Vein, or the Lateral Vein of the left ventricle LV. The leads are shown in a typical placement, lead 20 being an RA lead, lead 22 being an RV lead, and lead 24 being an LV lead inserted via the superior vena cava (SVC) into the coronary sinus ostium (CSO) located in the right atrium RA. The lead 24 is then advanced through the coronary sinus (CS), passes through the coronary venous system and its tip is positioned in a tributary of the coronary sinus, preferably the left posterior cardiac vein (PCV) or other appropriate coronary vein, with an associated tip electrode 30 being placed deep into the coronary vein of the left side of the heart. The phrase "coronary venous system" refers to the coronary sinus vein, great cardiac vein, left marginal vein, left posterior vein, middle cardiac vein, and/or small cardiac veins or any other cardiac vein accessible by the coronary sinus. From this location, the lead 24 can be used to stimulate the left ventricle (LV). Clearly, the lead 24 must follow a tortuous path in order for the tip electrode 30 to reach its intended destination. The lead 22 extends to a tip electrode 32 placed in the apex 34 of the RV and illustrates the typical position of a lead in the right ventricle. The lead 20 extends to a tip electrode 36 shown in the appendage of the RA and illustrates the typical position of the lead in the appendage of the right atrium. In this scenario, component 30 is typical of a pacing/sensing electrode of the LV lead 24, component 40 is typical of a shock electrode in the distal portion of the CS carried by the LV lead 24, component 42 is typical of a proximal shock coil of the RV lead 22, component 44 is typical of a distal shock coil of the RV lead 22, and component 46 is typical of a ring electrode of the RV lead 22.

Figure 2:
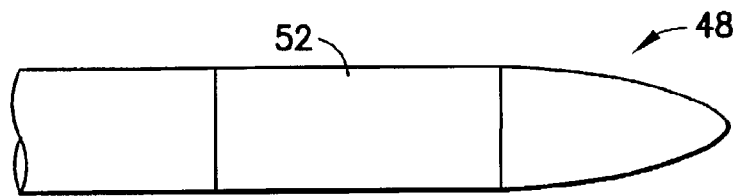
FIG. 2 is a detail elevation view illustrating the distal end of a known lead system.
Figure 3:
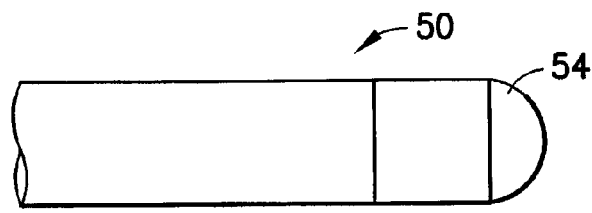
FIG. 3 is a detail elevation view illustrating the distal end of a another known lead system.

Current left heart pacing leads 48 (FIG. 2) and 50 (FIG. 3) whose stimulation electrodes are positioned in the coronary veins are simple in design. Lead 48 employs a ring electrode 52, which could also be a partial ring electrode and lead 50 employs a tip electrode 54. The difficulty with these known electrode designs is that they are not designed specifically for optimal cardiac stimulation thresholds in the coronary veins. More specifically, they are not able to provide electrical fields that are optimally directed towards excitable cardiac tissue. This condition is corrected by the present invention.

Figure 4:
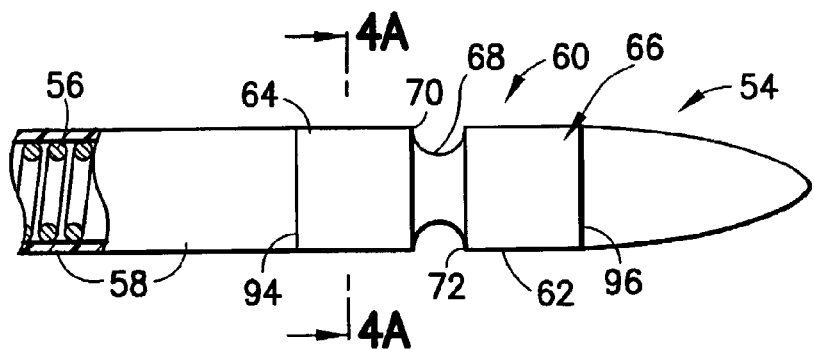
FIG. 4 is a detail elevation view illustrating the distal end of a lead system embodying the invention.
Figure 4A:
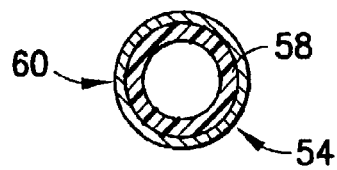
FIG. 4A is a cross-section view taken generally along line 4A—4A in FIG. 4.

As seen in FIGS. 4 and 4A, such an improved lead assembly 54 includes an electrical conductor 56 whose proximal end is coupled to an electrical connector at the pacemaker 26 in a known manner and as earlier illustrated in FIG. 1. An insulative sheath 58, preferably composed of silicone or polyurethane, covers the conductor and a distal electrode 60 composed of a biocompatible metal and/or alloy, for example, titanium nitride (TiN), is coupled to the distal end of the conductor 56 and has an outer surface 62 exposed through the exterior of the insulative sheath and positioned generally coaxial with the lead assembly. The outer surface of the distal electrode includes a material coating that exhibits low polarization and thereby enhances the electrical efficacy of the electrode. An electrode having such a characteristic may be comprised of a metallic substrate having an initially exposed outer surface substantially covered with a first inner layer of titanium nitride and a second outer layer of platinum black. In such an instance, the first inner layer of titanium nitride preferably has a thickness of less than about 15 microns and the second outer layer of platinum black overlying the layer of titanium nitride, similarly, preferably has a thickness of less than about 15 microns. A complete description of such an electrode is disclosed in earlier-mentioned U.S. patent application Ser. No. 09/707,706, filed Nov. 7, 2000, entitled "Stimulating Electrode Having Low Polarization and Method of Making Same". The outer surface 62 generally faces in directions transverse of the longitudinal axis of the lead assembly 54 and is generally parallel to the selected body tissue (for example, the vein 28 shown in FIG. 1), enabling it to direct a concentrated electrical charge toward the selected body tissue for its stimulation. The outer surface 62 has first and second longitudinally spaced cylindrical regions 64, 66 separated by an intermediate annular groove 68 to enhance tissue ingrowth and to create an environment of concentrated electrical charge directed at the selected body tissue. In this instance, the first and second cylindrical regions 64, 66 converge with the groove 68 at proximal and distal annular edges 70, 72, respectively, thereby creating the concentrated electrical charge.

Figure 5:
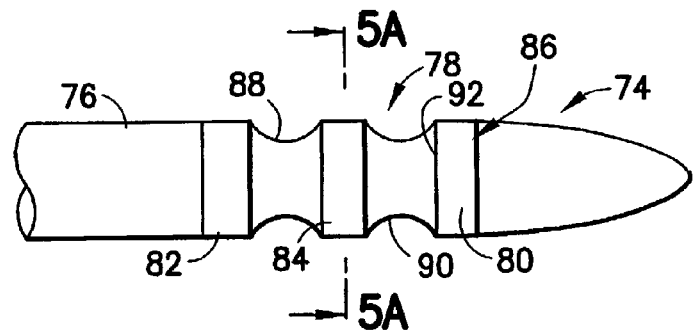
FIG. 5 is a detail elevation view illustrating the distal end of a modified lead system embodying the invention.
Figure 5A:
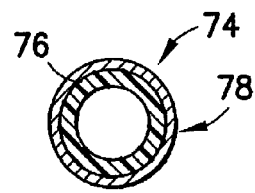
FIG. 5A is a cross-section view taken generally along line 5A—5A in FIG. 5.

Another embodiment of the invention is illustrated in FIGS. 5 and 5A according to which a modified lead assembly 74 similarly includes an electrical conductor (not shown in this instance) whose proximal end is coupled to an electrical connector at the pacemaker 26 in a known manner and as earlier illustrated in FIG. 1. An insulative sheath 76 covers the conductor and a distal electrode 78, similar in material to the electrode 60, is coupled to the distal end of the conductor and, similarly, has an outer surface 80 exposed through the exterior of the insulative sheath and positioned generally coaxial with the lead assembly. As in the previous embodiment, the outer surface 80 generally faces in directions transverse of the longitudinal axis of the lead assembly 74 and is generally parallel to the selected body tissue (for example, the vein 28 shown in FIG. 1), enabling it to direct a concentrated electrical charge toward the selected body tissue for its stimulation. In this instance, the outer surface 80 has first, second, and third longitudinally spaced cylindrical regions 82, 84, 86, separated by intermediate annular grooves 88, 90 to enhance tissue ingrowth and to create an environment of concentrated electrical charge directed at the selected body tissue. In this instance, also, the cylindrical regions 82, 84, 86 converge with the annular grooves 88 at a plurality of annular edges 92, respectively, thereby creating the concentrated electrical charge.

Turning back to FIG. 4, momentarily, it is seen that the distal electrode has discrete surfaces defined by the cylindrical regions 64, 66 which meet at interface boundaries 94, 96, respectively, thereby creating the concentrated electrical charge for the stimulation of the selected body tissue. A similar situation exists with respect to the lead assembly 74 of FIG. 5.

Figure 6:
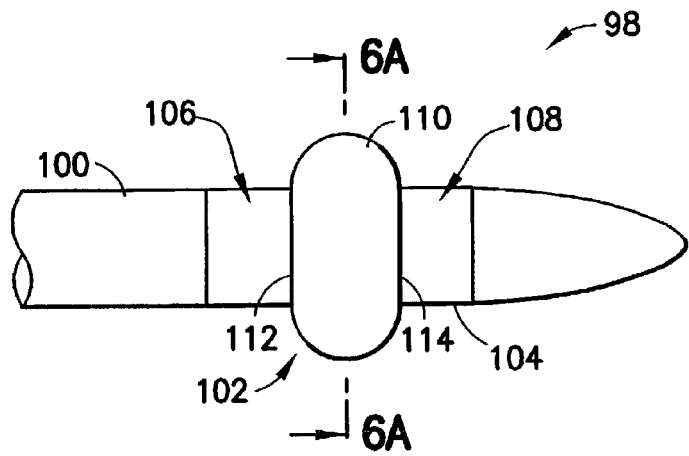
FIG. 6 is a detail elevation view illustrating the distal end of another modified lead system embodying the invention.
Figure 6A:
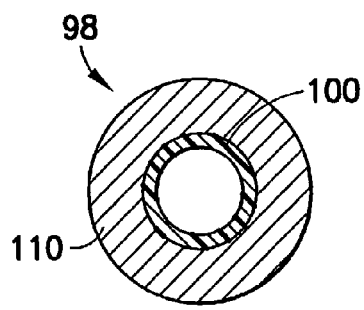
FIG. 6A is a cross-section view taken generally along line 6A—6A in FIG. 6.

Still another embodiment of the invention is illustrated in FIGS. 6 and 6A according to which a modified lead assembly 98 similarly includes an electrical conductor (not shown) and an insulative sheath 100 covering the conductor and a distal electrode 102, similar in material to the electrodes 60 and 78, is coupled to the distal end of the conductor and, similarly, has an outer surface 104 exposed through the exterior of the insulative sheath and positioned generally coaxial with the lead assembly. As in the previous embodiments, the outer surface 104 generally faces in directions transverse of the longitudinal axis of the lead assembly 98 and is generally parallel to the selected body tissue, enabling it to direct a concentrated electrical charge toward the selected body tissue for its stimulation. In this instance, the outer surface 104 has first and second longitudinally spaced cylindrical regions 106, 108 separated by an intermediate annular protuberance 110 to enhance tissue ingrowth and to create an environment of concentrated electrical charge directed at the selected body tissue. In this instance, also, the distal electrode has discrete surfaces which converge at annular corners 112, 114 represented, respectively, by the interface between the annular protuberance 110 and the cylindrical region 106 and by the annular protuberance and the cylindrical region 108. These annular corners 112, 114 serve to create the concentrated electrical charge required for stimulating the selected body tissue.

Figure 7:
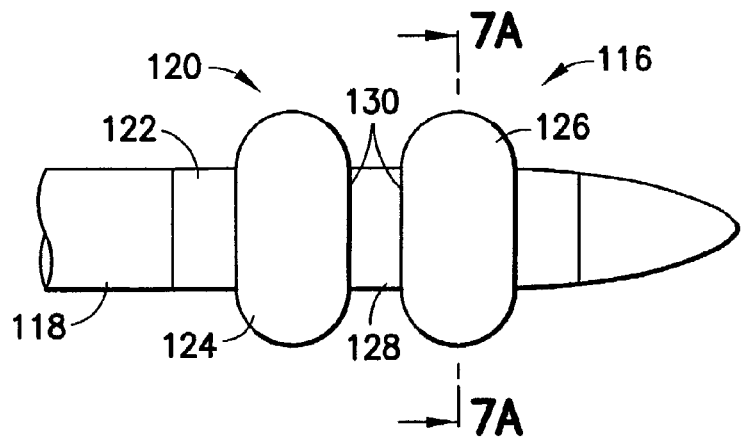
FIG. 7 is a detail elevation view illustrating the distal end of still another modified lead system embodying the invention.
Figure 7A:
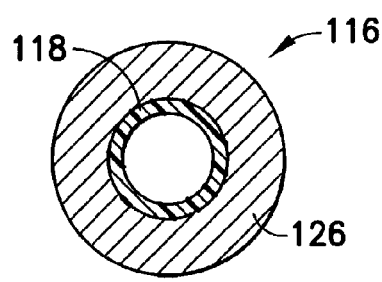
FIG. 7A is a cross-section view taken generally along line 7A—7A in FIG. 7.

Yet another embodiment of the invention is illustrated in FIGS. 7 and 7A according to which a modified lead assembly 116 similarly includes an electrical conductor (not shown) and an insulative sheath 118 covering the conductor and a distal electrode 120, similar in material to the electrodes 60, 78, and 102, is coupled to the distal end of the conductor and, similarly, has an outer surface 122 exposed through the exterior of the insulative sheath and positioned generally coaxial with the lead assembly. As in the previous embodiments, the outer surface 122 generally faces in directions transverse of the longitudinal axis of the lead assembly 116 and is generally parallel to the selected body tissue, enabling it to direct a concentrated electrical charge toward the selected body tissue for its stimulation. In this instance, the outer surface 122 has first and second longitudinally spaced annular protuberances 124, 126 separated by an intermediate cylindrical region 128 to enhance tissue ingrowth and to create an environment of concentrated electrical charge directed at the selected body tissue. In this instance, also, the distal electrode 120 has discrete surfaces which converge at a plurality of annular corners 130 represented, respectively, by the interfaces between the annular protuberances 124, 126 and the cylindrical regions 128. As previously, these annular corners 130 serve to create the concentrated electrical charge required for stimulating the selected body tissue.

Figure 8:
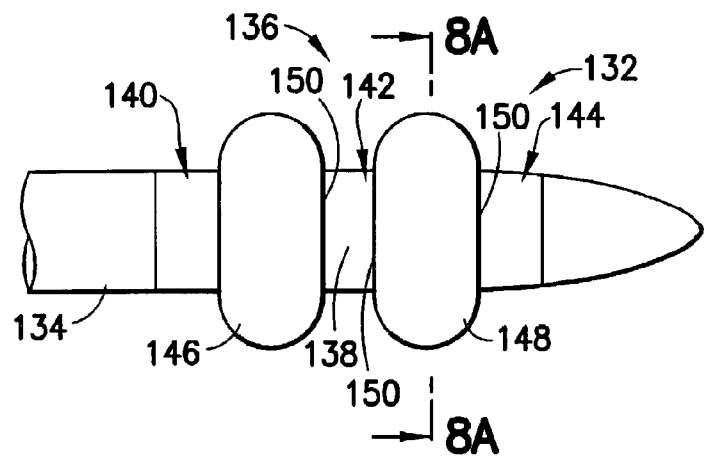
FIG. 8 is a detail elevation view illustrating the distal end of a modified lead system embodying the invention.
Figure 8A:
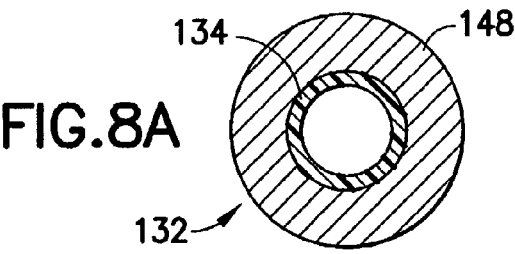
FIG. 8A is a cross-section view taken generally along line 8A—8A in FIG. 8.

Yet a further embodiment of the invention is illustrated in FIGS. 8 and 8A according to which a modified lead assembly 132 similarly includes an electrical conductor (not shown) and an insulative sheath 134 covering the conductor and a distal electrode 136, similar in material to the electrodes 60, 78, 102, and 120 is coupled to the distal end of the conductor and, similarly, has an outer surface 138 exposed through the exterior of the insulative sheath and positioned generally coaxial with the lead assembly. As in the previous embodiments, the outer surface 138 generally faces in directions transverse of the longitudinal axis of the lead assembly 116 and is generally parallel to the selected body tissue, enabling it to direct a concentrated electrical charge toward the selected body tissue for its stimulation. In this instance, the outer surface 138 has first, second, and third longitudinally spaced cylindrical regions 140, 142, 144 separated, respectively, by intermediate annular protuberances 146, 148 to enhance tissue ingrowth and to create an environment of concentrated electrical charge directed at the selected body tissue. In this instance, also, the distal electrode 132 has discrete surfaces which converge at a plurality of annular corners 150 represented, respectively, by the interfaces between the annular protuberances 146, 148 and the cylindrical regions 140, 142, 144. As previously, these annular corners 150 serve to create the concentrated electrical charge required for stimulating the selected body tissue.

Figure 9:
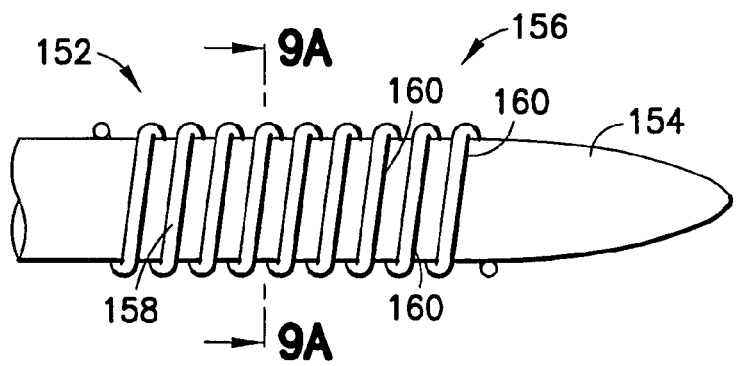
FIG. 9 is a detail elevation view illustrating the distal end of a modified lead system embodying the invention.
Figure 9A:
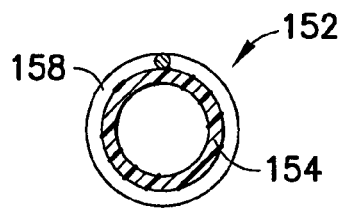
FIG. 9A is a cross-section view taken generally along line 9A—9A in FIG. 9.

Yet a further embodiment of the invention is illustrated in FIGS. 9 and 9A according to which a modified lead assembly 152 similarly includes an electrical conductor (not shown) and an insulative sheath 154 covering the conductor and a distal electrode 156, similar in material to the electrodes 60, 78, 102, 120, and 136 is coupled to the distal end of the conductor. In this instance, the distal electrode 156 is a coil conductor 158 coaxial with the lead assembly 152 and overlying the insulation sheath 154 and, as with the earlier-described distal electrodes, is coated with a suitable type of material, as earlier mentioned, that exhibits low polarization and thereby enhances the electrical efficacy of the electrode. As in the previously described embodiments, the outer surface of the coil conductor 158 generally faces in directions transverse of the longitudinal axis of the lead assembly 152 and is generally parallel to the selected body tissue, enabling it to direct a concentrated electrical charge toward the selected body tissue for its stimulation. In this instance, also, the distal electrode 152 in the form of the coil conductor 158 has discrete surfaces which converge at a plurality of annular corners 160 represented, respectively, by the interfaces between the coil conductor 158 and the insulation sheath 154. As previously, these annular corners 160 serve to create the concentrated electrical charge required for stimulating the selected body tissue.

Figure 10:
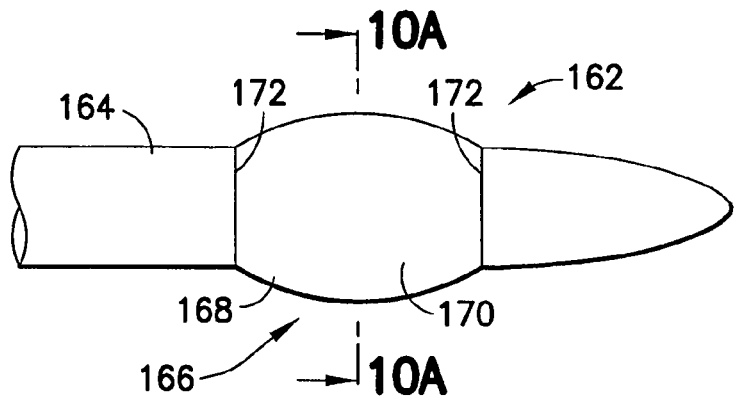
FIG. 10 is a detail elevation view illustrating the distal end of a modified lead system embodying the invention.
Figure 10A:
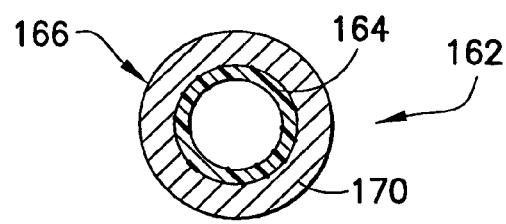
FIG. 10A is a cross-section view taken generally along line 10A—10A in FIG. 10.

Still another embodiment of the invention is illustrated in FIGS. 10 and 10A according to which a modified lead assembly 162 similarly includes an electrical conductor (not shown) and an insulative sheath 164 covering the conductor and a distal electrode 166, similar in material to the electrodes 60, 78, 102, 120, 136, and 156 is coupled to the distal end of the conductor and, similarly, has an outer surface 168 exposed through the exterior of the insulative sheath and positioned generally coaxial with the lead assembly. As in the previous embodiments, the outer surface 168 generally faces in directions transverse of the longitudinal axis of the lead assembly 162 is generally parallel to the selected body tissue, enabling it to direct a concentrated electrical charge toward the selected body tissue for its stimulation. In this instance, the outer surface 168 has an annular protuberance 170 to produce an environment of concentrated electrical charge directed at the selected body tissue. In this instance, also, the discrete outer surface 168 of the annular protuberance 170 converges at a pair of annular corners 172 represented, respectively, by the interfaces between the annular protuberance and the insulative sheath 164. As previously, these annular corners 172 serve to create the concentrated electrical charge required for stimulating the selected body tissue.

Figure 11:
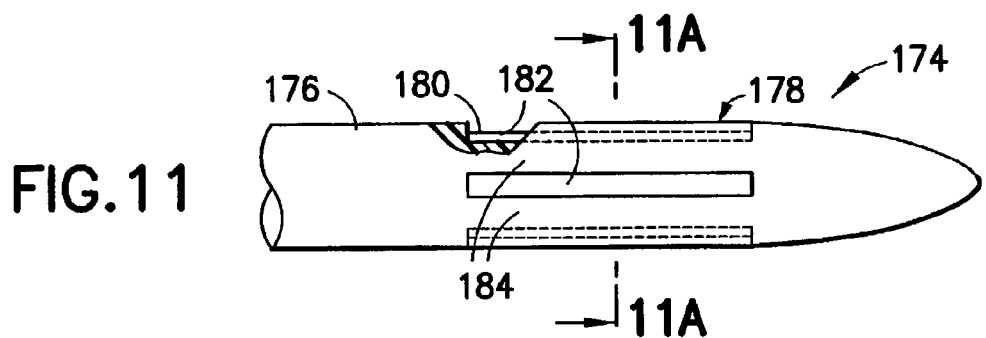
FIG. 11 is a detail elevation view illustrating the distal end of a modified lead system embodying the invention.
Figure 11A:
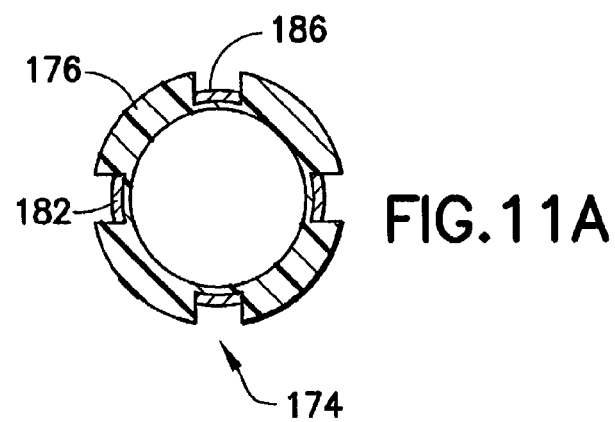
FIG. 11A is a cross-section view taken generally along line 11A—11A in FIG. 11.
Figure 12:
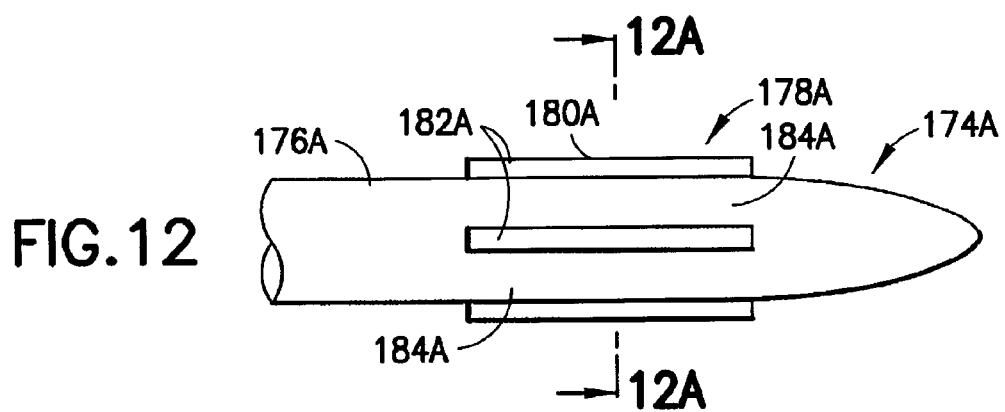
FIG. 12 is a detail elevation view illustrating the distal end of a modified lead system embodying the invention.
Figure 12A:
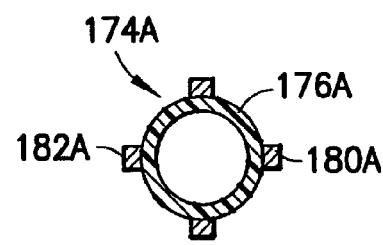
FIG. 12A is a cross-section view taken generally along line 12A—12A in FIG. 12.
Figure 13:
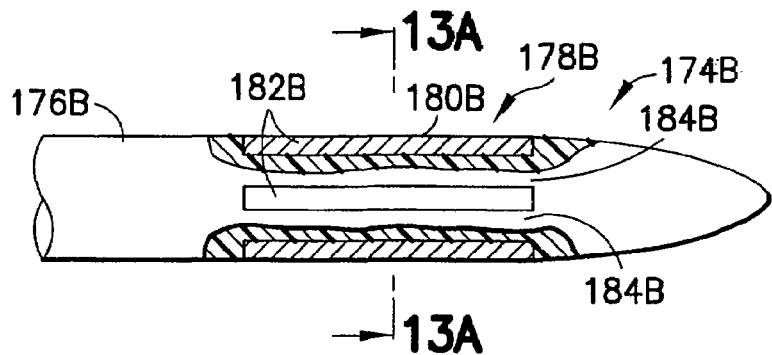
FIG. 13 is a detail elevation view illustrating the distal end of a modified lead system embodying the invention.
Figure 13A:
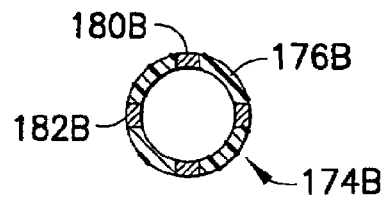
FIG. 13A is a cross-section view taken generally along line 13A—13A in FIG. 13.

Yet another embodiment of the invention is illustrated in FIGS. 11 and 11A according to which a modified lead assembly 174 similarly includes an electrical conductor (not shown) and an insulative sheath 176 covering the conductor and a distal electrode 178, similar in material to the electrodes 60, 78, 102, 120, 136, 156, and 166, is coupled to the distal end of the conductor and, similarly, has outer surfaces 180 exposed through the exterior of the insulative sheath and positioned generally coaxial with the lead assembly. As in the previous embodiments, the outer surfaces 180 generally face in directions transverse of the longitudinal axis of the lead assembly 174 and are generally parallel to the selected body tissue, enabling the distal electrode 178 to direct a concentrated electrical charge toward the selected body tissue for its stimulation. In this instance, the distal electrode 178 includes at least two longitudinally extending circumferentially spaced rectangular electrode members 182 thereon, each being composed of a biocompatible metal and/or alloy and coated of a material that exhibits low polarization and thereby enhances the electrical efficacy of the electrode. Additionally, the construction of the lead assembly 174 also includes at least two longitudinally extending circumferentially spaced insulative strips 184 thereon circumferentially intermediate the rectangular electrode members. Indeed, the insulative strips 184 are merely extensions or isthmus' of the insulative sheath 176. In the instance of FIGS. 11 and 11A, outer surfaces 186 of the rectangular electrode members 182 are recessed relative to the insulative sheath. A further variation of the construction illustrated in FIGS. 11 and 11A is illustrated in FIGS. 12 and 12A with reference numerals for each of the components provided with the suffix "A" and, in this instance, outer surfaces 180A of the rectangular electrode members 182A are elevated relative to the insulative sheath 176A. Yet another variation of the construction illustrated in FIGS. 11 and 11A is illustrated in FIGS. 13 and 13A with reference numerals for each of the components provided with the suffix "B" and, in this instance, outer surfaces 180B of the rectangular electrode members 182B are flush with the insulative sheath 176B.

In each instance, the interface between the rectangular electrode members 182, 182A, 182B and the insulative sheath 176, 176A, 176B, respectively serves to create the concentrated electrical charge required for stimulating the selected body tissue.

Figure 14:
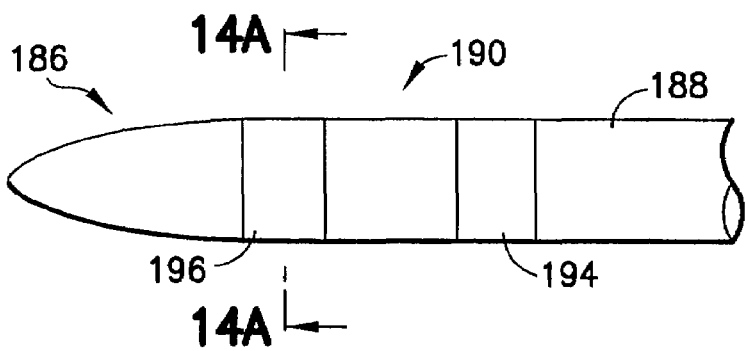
FIG. 14 is a detail elevation view illustrating the distal end of a modified lead system embodying the invention.
Figure 14A:
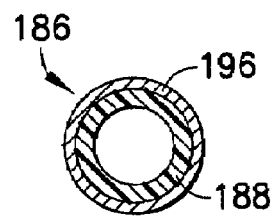
FIG. 14A is a cross-section view taken generally along line 14A—14A in FIG. 14.
Figure 15:
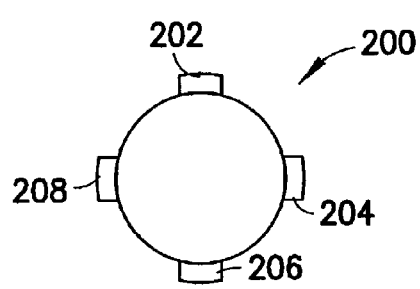
FIG. 15 is a diagrammatic end elevation view of a lead assembly to be operated according to the invention.

Yet another embodiment of the invention is illustrated in FIGS. 14 and 14A according to which a modified lead assembly 186 similarly includes an electrical conductor (not shown) and an insulative sheath 188 covering the conductor and a distal electrode 190, similar in material to the electrodes 60, 78, 102, 120, 136, 156, 166, and 178, is coupled to the distal end of the conductor and, similarly, has an outer surface exposed through the exterior of the insulative sheath and positioned generally coaxial with the lead assembly. However, in this instance, the outer surface has at least first and second longitudinally spaced cylindrical regions 194, 196, each pair of regions being separated by the insulative sheath 188, each cylindrical region serving to enhance tissue ingrowth and to create an environment of concentrated electrical charge directed at the selected body tissue. As in the previous embodiments, the cylindrical regions 194, 196 generally face in directions transverse of the longitudinal axis of the lead assembly 186 and are generally parallel to the selected body tissue, enabling them to direct a concentrated electrical charge toward the selected body tissue for its stimulation. In this instance, also, the cylindrical regions 194, 196 Interface with the insulative sheath 198 and thereby create the concentrated electrical charge required for stimulating the selected body tissue.

Figure 16:
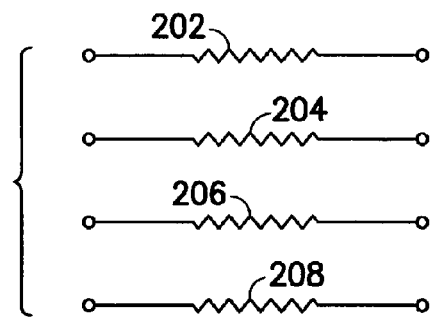
FIGS. 16, 17, 18, 19A, and 19B are simple electrical schematic representations for describing various operations according to the invention.
Figure 17:
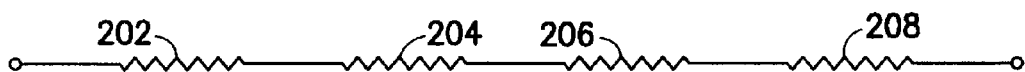
Figure 18:
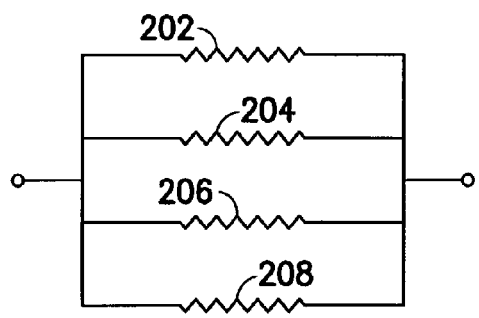
Figure 19A:
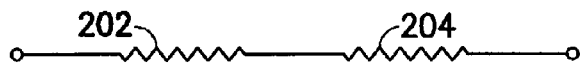
Figure 19B:
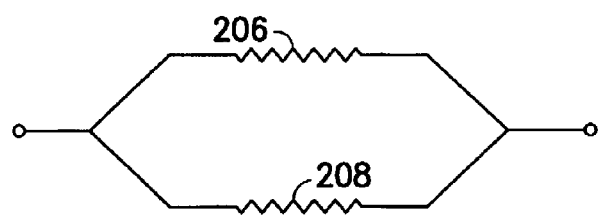

An additional feature of the invention will now be described with the aid of FIGS. 15, 16, 17, 18, 19A, and 19B. In those instances in which lead assemblies of the nature described have multiple electrodes, it is possible to operate those electrodes individually or in concert to achieve a desired result. Such a typical lead assembly 200 is diagrammatically illustrated in FIG. 15 which includes electrodes 202, 204, 206, and 208. Thus, as seen in FIG. 16, a lead assembly is depicted in which the electrodes 202, 204, 206, and 208 are electrically independent while in FIG. 17, a lead assembly is depicted in which the electrodes 202, 204, 206, and 208 are electrically in series. In FIG. 18, the electrodes 202, 204, 206, and 208 are electrically in parallel, and in FIG. 19A, at least two of the electrodes, namely 202 and 204, are electrically in series while in FIG. 19B, at least two of the electrodes, namely 206 and 208 are electrically in parallel.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A lead assembly for a body implantable medical system adapted to transmit electrical signals between a proximal end portion of the lead assembly and a distal end portion of the lead assembly to thereby stimulate selected body tissue, the lead assembly having a longitudinal axis and comprising:

an electrical conductor extending between a proximal end and a distal end;

an insulative sheath covering the conductor;

an electrical connector coupled to the proximal end of the conductor for releasable attachment to a stimulating pulse generator; and a distal electrode coupled to the distal end of the conductor and having an outer surface exposed through the exterior of the insulative sheath generally coaxial with the lead assembly and generally facing in directions transverse of the longitudinal axis of the lead assembly and generally parallel to the selected body tissue for directing a concentrated electrical charge toward the selected body tissue for the stimulation thereof;

wherein the outer surface has first and second longitudinally spaced cylindrical regions separated by an intermediate annular groove to enhance tissue ingrowth and to create an environment of concentrated electrical charge directed at the selected body tissue; and wherein the first and second longitudinally spaced cylindrical regions converge with the intermediate annular groove at proximal and distal annular edges having substantially small radii to create a concentrated electrical charge at the selected body tissue.

2. The lead assembly as set forth in claim 1:
wherein the proximal and distal annular edges comprise an annular corner thereby creating the concentrated electrical charge.

3. The lead assembly as set forth in claim 1:
wherein the distal electrode has a first discrete surface and the insulative sheath has a second discrete surface; and
wherein the first and second surfaces meet at an interface boundary thereby creating the concentrated electrical charge.

4. The lead assembly as set forth in claim 1:
wherein the distal electrode is composed of a biocompatible metal and/or alloy, and whose outer surface includes a material coating that exhibits low polarization and thereby enhances the electrical efficacy of the electrode.

5. The lead assembly as set forth in claim 1:
wherein the insulative sheath is composed of at least one of silicone and polyurethane.

6. The lead assembly as set forth in claim 1:
wherein the outer surface has first, second, and third longitudinally spaced cylindrical regions separated, respectively, by first and second intermediate annular grooves to enhance tissue ingrowth and to create an environment of concentrated electrical charge directed at the selected body tissue.

7. The lead assembly of claim 1, wherein a longitudinal length of the intermediate annular groove is sufficiently small to enhance tissue ingrowth and to create an environment of concentrated electrical charge directed at the selected body tissue.

8. A lead assembly for a body implantable medical system, the lead assembly comprising:
   a lead housing;
   an electrical conductor housed in the lead housing;
   an electrical connector coupled to the conductor and configured for releasable attachment to a stimulating pulse generator; and
   an electrode coupled to the electrical conductor, the electrode defining an outer surface, the outer surface having first and second longitudinally spaced cylindrical regions converging with an intermediate annular groove at proximal and distal annular edges, and the proximal and distal annular edges having substantially small radii to create an environment of concentrated electrical charge directed at selected body tissue.

9. The lead assembly of claim 8, wherein the proximal and distal annular edges comprise annular corner.

10. The lead assembly of claim 8, wherein a longitudinal length of the intermediate annular groove is sufficiently small to enhance tissue ingrowth and to create an environment of concentrated electrical charge directed at the selected body tissue.

* * * * *